United States Patent [19]
Gopalan et al.

[11] Patent Number: 5,658,571
[45] Date of Patent: Aug. 19, 1997

[54] PROCESS FOR EXTRACTION AND USE OF FENUGREEK (TRIGONELLA FOENUMGRAECUM)

[75] Inventors: Gudalar Gopalan, Madras; Vivek Narayan Pai; Pradeep Narayan Pai, both of Bombay; Ravindran Gopalan, Madras, all of India

[73] Assignee: Vitamed Remedies Private Limited, Madras, India

[21] Appl. No.: 561,711

[22] Filed: Nov. 22, 1995

[30] Foreign Application Priority Data

Nov. 24, 1994 [IN] India ............................ 1162/M/94

[51] Int. Cl.$^6$ ........................ A61K 35/78; A23L 1/015
[52] U.S. Cl. .................... 424/195.1; 426/425; 426/427; 426/428; 426/429; 426/430; 426/417; 426/629
[58] Field of Search ............................ 426/531, 533, 426/534, 550, 425, 427, 428, 429, 430, 417, 629; 424/195.1

[56] References Cited

U.S. PATENT DOCUMENTS 3,869,558  3/1975  Hampton et al. ................. 426/443

FOREIGN PATENT DOCUMENTS 0441672  8/1991  European Pat. Off. .
8505251  12/1985  WIPO .................. A23L 1/20

OTHER PUBLICATIONS

Ali, L. et al. "Characterization of the hypoglyamie effects . . . " Research Division, Bangladesh Institute of Research & Rehabilitation Abstract 123:218164, 1995.

Petit, P. et al. "Effects of a Fenugreek . . . " Lab. Pharmacol., Fac. Med, Montpellier, 34060 FR Abstract 119:108770.

Primary Examiner—Mary E. Mosher
Assistant Examiner—Ali R. Salimi
Attorney, Agent, or Firm—Ladas & Parry

[57] ABSTRACT

A process for preparing debitterised powder of the seed of the plant Fenugreek (Trigonella Foenumgraecum). The debitterised powder of the seed and formulations containing the debitterised powder of the seed of Fenugreek are useful as fiber supplements. Guar gum and bran can be blended with the debitterised powder of the seed of Fenugreek to prepare formulations which can be used as fiber supplements.

23 Claims, No Drawings

PROCESS FOR EXTRACTION AND USE OF FENUGREEK (*TRIGONELLA FOENUMGRAECUM*)

FIELD OF THE INVENTION

This invention relates to a process for the debitterisation of the seed of Fenugreek (*Trigonella foenumgraecum*), the debitterised seed and formulations containing the debitterrised seed which are useful as fiber supplements. The debitterised seed as well as the formulations according to the present invention are useful for the prevention and treatment of certain chronic diseases such as diabetes, coronary artery diseases, diverticultis, cancer of the colon, piles, fissures, chronic constipation and the like. The formulations serve as a source of highly concentrated dietary fiber and can be used as a food supplement.

BACKGROUND OF THE INVENTION

The diet of an individual should contain required quantities of fibrous materials so as to maintain fiber balance and good health. The deficiency of the required quantity of fibrous materials in the daily diet of an individual may cause problems such as diabetes, coronary artery diseases, diverticulosis, cancer of the colon, piles, fissures, chronic constipation and the like. Fiber is normally obtained from food. Dietary fiber available in plant cell walls escapes digestion by the enzymes present in the gastrointestinal tract. The chief components of dietary fiber are cellulose, lignins and non cellulosic polysaccharides. Lignin is a non-carbohydrate dietary constituent which is totally indigestible. Polysaccharides belong to two categories (i) Cellulose—it is like lignins in that it cannot be easily digested and (ii) non cellulosic polysaccharides, which comprise chiefly hemicellulose, pectin, plant gums and mucilages. While proteins, fats and carbohydrates have been studied extensively, the unabsorbable fiber portion of food has almost been ignored, probably because it is indigestible, not assimilated in the body, is non-caloric and of negligible nutrient value.

The modern day increase in the incidence and severity of diseases like hypertension, diabetes, cancer of the large intestines, irritable bowel syndrome and heart attacks have been linked to lack of fiber in the diet. The causes seem to be the changing food habits from natural foods to Western type diets of refined foods. Consumption of unrefined highly soluble fiber carbohydrate rich foods protect against many Western ailments like colon cancer, diverticular diseases, gallstones, obesity, in addition to constipation. Although the traditional Indian may be consuming plenty of fiber rich foods, those living in urban areas especially the affluent may be ingesting less than the required quantity of dietary fiber rich food. This is reflected in the higher incidence of heart ailments, diabetes and constipation in the cities as compared to the villages.

The present day diet contains tasty refined (that is fiber depleted) carbohydrate foods, especially sucrose which requires little chewing at the expense of its unrefined counterpart starch. Diets rich in sugars and fats are low in starch content and hence low in insoluble fiber.

The switching over to modern diets containing high amounts of sugar and fat presently contribute to 55 to 60% of the daily calories as compared to 15 to 20% a century ago. The situation is further complicated due to the inconvenience and monotony of ingesting fibrous products. The increasing cost of fibrous food materials such as fruits, vegetables and their non-availability during off and lean seasons also contributes to the development of fiber deficiency and low levels of fibrous materials in the daily diet. Some fiber containing foods are unprocessed seeds and grains (legumes and cereals). Pulses (legumes as they are called) are a rich source of protein in the diet. Pulses are also edible seeds of various leguminous plants, for example, chickpeas, lentils, beans, etc. In vegetarian diets, pulses find an important place as a source of protein. Pulses are also rich in "B" Vitamins, so they can contribute significantly to vitamin intake. Nuts are also rich sources of fiber but are high in fat and calories.

Daily fiber intake of an individual consequently becomes inadequate resulting in serious illness such as diabetes, coronary artery diseases, diverticulosis, cancer of colon, piles, fissures and chronic constipation. The above conditions need treatment but also need prevention.

Benefits of taking fibrous materials in the daily diet of an individual are very well known world over. There is an increasing need for dietary products containing high mounts of fiber to meet the increased daily fiber requirements.

When one considers developing a fibrous dietary product containing a high percentage of fibrous materials it is essential to ensure that the product used as a food supplement would provide a high quantity of fiber including soluble fiber in a palatable and easy to take form.

SUMMARY OF THE INVENTION

The main object of the present invention is therefore to provide a debitterised seed of the plant Fenugreek (*Trigonella foenumgraecum*) and formulations containing the debitterised seed which will provide a high quantity of fibrous materials for an individual. The debitterised seed according to this invention is in the form of a powder.

Another objective is to provide a process for preparing debitterised seed of Fenugreek.

Yet another object of the present invention is to provide a formulation containing high quality fibers which is a dry concentrate, which can be taken by itself or can be incorporated easily into cooked or uncooked food, or added to water, soups or other liquids. The formulation should also be tasty.

Still another object of the present invention is to provide a process for the preparation of a formulation which is palatable, easy to ingest, and ready to take.

Processes for debitterising the seed of Fenugreek are known. The processes that are known are the ones used for extracting oil and oleoresins. In the known oleoresin extraction processes, the product turns from dark brown to black when it comes into contact with water in any form. In this invention, unlike the known oleoresin extraction processes, the extraction of the powder of the seed of Fenugreek occurs without being directly contacted with steam.

DETAILED DESCRIPTION OF THE INVENTION

The invention is based on the finding that when powder of the seed of Fenugreek (*Trigonella Foenumgraecum*) is treated in the manner according to the present invention, the bitterness present in the seeds is unexpectedly removed and the resultant powder product contains a high percentage of fiber which can be taken as a dietary fibrous food supplement. The bitterness usually found in the powder of the seeds of Fenugreek (*Trigonella Foenugraecum*) is surprisingly absent in the resulting powder product. Thus, the powder is made palatable. Further, the inventors have also observed that if the seeds of Fenugreek treated according to the process of the present invention are mixed with guar gum (*Cyamoopsis Tetragonolobus*) and bran, this results in a synergistic formulation having a very high content of fiber and is also tasty. Guar gum (*Cyamoopsis Tetragonolobus*) is the commercially separated product of the endosperm of the Indian cluster bean. The latter is a legume which has its main storage of polysaccharides in the form of galactomannans. Most guar gum contains 80% galactomannan by weight and less than 10% mineral water by weight. Bran is the outer fibrous layer of cereal grains and is the product of flour milling. It comprises approximately 12% by weight of cereal grains. It has cellulose, hemicellulose and other polysaccharides, protein, minerals and many parts of the germ of the embryo. Bran provides a beneficial laxative action. The soluble fiber provided by bran is 13% by weight. The seed treated according to the process of the present invention has water holding capacity and cationic exchange properties.

The fiber content of the daily diet of an individual can be conveniently raised to the level required by including the powder of the debitterised seed or one of the formulations of the present invention in the daily diet. This required level can be achieved both in healthy persons as well as in diseased and/or fiber deficient individuals.

The plant Fenugreek (*Trigonella Foeumgraecum*) is grown in India, Mediterranean countries and the Near East. The plant has many uses. The tender leaves are used as vegetables and its seeds as condiments. Debitterisation of the seed does not compromise its hypocholesterolemic and hypoglycemic properties. The analysis of the seed components reveals that seeds of Fenugreek contain fiber 48% by weight; steroid saponins 4.8% by weight; lipids 7% by weight and trigonelline 0.3% by weight. The fiber includes mucilage 20% by weight, hemicellulose 17.3% by weight, cellulose 8.2% by weight and lignin 2.5% by weight.

Accordingly, the present invention provides a process for the debitterisation of the seed of the plant Fenugreek (*Trigonella Foenumgraecum*) which makes it useful as a dietary fiber food. The process comprises:

(i) loading a powder of ground seed of Fenugreek (*Trigonella Foerumgraecum*) into a reactor vessel comprising an extractor containing filtering material and having a jacket for passing stem;

(ii) soaking the powder with a solvent capable of extracting fat and compounds and components that cause bitterness from the powder by passing the solvent through the extractor to wet the powder;

(iii) warming the reactor vessel slowly by passing steam through the jacket without contacting the powder in the extractor, wherein the powder along with the solvent which may remain with the powder is treated by passing the steam through the jacket;

(iv) separating the solvent from the powder; and (v) discharging the powder from the extractor.

The process further comprises:

(a) cleaning the seed of the plant Fenugreek (*Trigonella Foenumgraecum*) to remove all the visible extraneous materials such as packaging materials, gunny wastes, dust and the like; (b) grinding the clean seed to a mesh size in the range of 30 to 50 BSS (British Standard Sieve) mesh; (c) loading the powder into a reactor vessel containing an extractor filled with filtering materials and having a jacket for passing stem; (d) soaking the resulting powder with a solvent capable of extracting fat and compounds and components that cause bitterness from the powder by passing the solvent through the extractor concurrently for effecting slow and uniform wetting of the powder; (e) warming the reactor vessel slowly by passing steam through the jacket without contacting the material present in the extractor, (f) treating the powder along with the solvent which may remain with the powder by passing the steam through the jacket. The duration of the steam treatment may range from half an hour to one hour; (g) separating the solvent by conventional methods and (h) if desired, recovering the solvent and recirculating the recovered solvent into the extractor, or if desired, adding fresh solvent to the extractor and (i) discharging the powder, drying and pulversising to a particle size ranging from 60 to 80 BSS (British Standard Sieve) mesh.

Examples of extractors that can be used are extractors that have false bottoms; rotary type extractors and continuously circulating type extractors.

According to the process of this invention, powder is loaded in the extractor and the solvent is passed through the extractor. The solvent is passed through the extractor in such a way that slow and uniform wetting of the powder is achieved. This may be achieved by spraying the solvent at the top of the extractor.

The solvent used may be selected from ethylene chloride, methylene chloride, acetone, hexane, alcohol, isopropyl alcohol, solvent ether, and the like. More than one type of solvent can be used in the process. The components or compounds of the seed of Fenugreek which cause bitterness are Trigonelline alkoloid oil, resins and glycocides. The solvent will be able to extract all the above components and compounds in order to reduce the bitterness. The solvent should also be capable of extracting fat from the powder. The solvent may also be capable of extracting fibrous materials from the powder. If such a solvent is used, the solvent will not leave a powder lacking the appropriate fiber content by virtue of the extraction of the fibrous materials when the powder is soaked. In the end, the debitterised powder will not lose any fiber content as a result of the powder being soaked with a solvent capable of extracting fibrous materials from the powder. What actually comes out as a result of soaking are some gummy substances which will not reduce the fiber content. The parameters that are used in determining the solvents that can be used are:

a) The solvent should be able to extract the maximum amount of bitterness and fat from the powder, b) The solvent should not affect the color of the end product (i.e the powder which is creamish yellow to light brown in color), c) The solvent should be permitted for use in edible products, d) The solvent should be cost effective, economical and the use of which should not make the end product costly.

The filtering materials used in the extractor are selected so as to be capable of allowing uniform percolation of solvent throughout the filtering material so that slow and uniform wetting of the powder is achieved. It is preferred that the extractor be filled with filtering material. The filtering materials may be selected from coir; drill; cloth, for example, filtering cloth or polypropylene cloth; materials embedded with cotton pads, and the like. Coir is a product produced from the outer coverings of coconuts. Coir is in the form of fibers and is useful as a filter material. Drill is a thick cotton cloth.

The temperature of the extractor is to be maintained in a range of 45° to 80° C., preferably in the range of 45° to 60° C. This temperature range is maintained when the reactor vessel is warmed by passing the steam through the jacket. Steps (ii) and (iii) occur at the same time; as do steps (d), (e) and (f).

Steps (ii)–(iv) and (d)–(h) can be repeated until the extraction is complete. The steps are repeated as necessary until the extraction is complete that is when the color of the solvent is the same or nearly the same as the original solvent. Fresh solvent may be used or the solvent drained from the extractor can be reintroduced into the extractor to soak the powder. The treatment of the powder may be continued until all the undesired materials are removed from the powder. After the extraction is complete, the solvent taken from the extractor may be recycled for the extraction of a fresh batch of the powder. The soaking in steps (ii) and (d) preferably consists of repeated washes, preferably 5 to 6 washes for a period ranging from one to two hours each preferably, one hour each. The entire process can be completed in about 8 to 12 hours, preferably 10 to 12 hours.

If steam is passed through the reactor rather than through the jacket of the extractor this results in a change of color of the debitterised powder to deep brown which is not suitable for consumption and appearance. In applicants process, direct contact of water with the powder of the seed of Fenugreek is avoided. In this invention steam is passed, through the jacket of the reactor so as to avoid direct contact of the steam with the debitterised powder and the solvent. Thus, the powder and the solvent are heated indirectly. In addition, air can also be passed through the reactor for recovering the solvent trapped inside the powder.

After the powder has been treated it can be manually removed or discharged from the extractor. After the powder is removed from the extractor, it can be dried and pulverised to a particle size ranging from 60 to 80 BSS. The powder is then tested for its bitterness and it is normally found that the bitterness is reduced considerably to the extent that it is palatable. The bitterness may be tested by using the Liebermann Burchard Color Reaction Test. The resulting product can be used as dietary fibrous food supplement.

According to another feature of the invention there is provided a process for the preparation of formulations which comprises mixing the powder of the seed of the plant Fenugreek (*Trigonella Foenumgraecum*) treated as described above with guar gum (*Cyamoopsis Tetragonolobus*) and bran. The amount of the debitterised powder of the seed of Fenugreek (*Trigonella Foenumgracum*) in the formulation may range from 40% to 80% by weight. The amount of guar gum may range from 15% to 30% by weight. The bran used may be selected from rice bran, wheat bran and the like and the amount may range from 5% to 10% by weight. During the mixing, additional ingredients such as coloring and/or flavoring agents may be added. Ingredients such as vitamins, minerals and proteins may also be incorporated during the mixing. Examples of coloring agents that may be used are orange, sunset yellow, tonceu orange, tratraine and anato. Anato is a natural color derived from the extraction of the outer coating of seeds of the Anato tree (Bix Orenella—L). The amount of coloring agent may be from 0.25 to 0.50% by weight. Examples of flavoring agent that may be used are orange, pineapple, grape or lemon. The amount of flavoring agent may be from 1 to 2% by weight. Examples of vitamins and minerals that may be used are the "B" complex vitamins, and salts of iron, calcium and zinc. The mount of vitamins may range from 0.05% to 0.75% by weight. Proteinaceous materials such as soya and groundnut may be added. The amount of proteinaceous materials may be from 3 to 8% by weight.

The moisture content of the formulation may range from 3% to 8% by weight. The moisture level may be kept preferably at 3% by weight. This may be checked during the process periodically. The mixing of the ingredients may be effected in a blender for uniform mixing. The blender employed may be a ribbon blender or double core blender or the like. The blending may be effected for a period ranging from one to three hours depending upon the consistency required. In some cases, the above three ingredients are mixed together to prepare a formulation having a suitable viscosity to ensure that it can be used as a drink.

The formulation of the present invention is not a simple admixture of the ingredients resulting in a product having their aggregate properties. The powder of debitterised seed of Fenugreek obtained according to the process of this invention when mixed with guar gum and bran results in a synergistic formulation having enhanced fiber content. The formulation is synergistic having properties which are unexpected and different from those possessed by the ingredients employed.

The formulation is synergistic because three fiber sources are blended. Each fiber source has different physiological and pharmacological (pharmacokinetic) properties. The synergistic effect is much more than each fiber source in terms of total effect. The content of total fiber and soluble fiber is much more in the synergistic formulation as compared to each individual fiber source in the formulation. Ultimately, because of the different physiological and pharmacological properties of different fiber sources, the total effect is synergistic and non additive. The data given below evidences this:

| PRODUCT | INSOLUBLE FIBER % by weight | SOLUBLE FIBER % by weight | TOTAL DIETARY FIBER % by weight |
| --- | --- | --- | --- |
| SYNERGISM | | | |
| FENUGREEK | 28 | 20 | 48 |
| GUARGUM | TRACE | 80 | 80 |
| WHEAT BRAN | 100 | TRACE | 100 |
| FIBERNAT* | 22 | 27 | 49 |

*FIBERNAT is a formulation according to this invention containing 80% by weight the of debitterised powder of the seed of Fenugreek; 15% by weight of guar gum and 5% by weight of bran.

From the table it can be seen that:

a) The absence of a fraction of dietary fiber in one component is compensated by another component that contains larger amounts of that fraction.

b) Since soluble and insoluble fractions of fiber have specific actions in the human body, a formulation containing a blend of the different types of dietary fiber would be superior in helping one to obtain all the benefits of fiber rather than single component fiber formulations containing only one type of dietary fiber.

c) With regard to physical properties, soluble fiber gels very quickly while insoluble fiber tends to settle down when mixed with water. A blend of these two fractions in the proper proportions would keep them in solution.

d) With regard to taste and flavor, each of the three components have a characteristic taste and flavor of their own but when mixed with each other as in the formulation, the resultant taste and flavor is quite different from the taste and flavor of any single component.

e) It may be noted that undesirable side effect of one component is corrected by another and thus the combination has a salutary effect.

Due to the synergistic effect of the ingredients whatever little bitterness remains in the treated seed of Fenugreek (*Trigonella Foenumgraecum*), completely disappears and the formulation becomes more palatable and very tasty.

When the debitterised powder of the seed of Fenugreek or formulation containing debitterised powder of Fenugreek Seed, guar gum and bran is added to water, the fiber contained in it swells and it becomes a jelly within a very short period of time.

The debitterised seed powder and formulations of the present invention containing the debitterised seed powder aids in the enhancement of easy bowel movements. It enhances soft and bulky stools, prevents intercolonic pressures and spasms. This helps in avoiding constipation thereby preventing occurrences of benign and malignant tumors in the colon and rectum. Further, the seed treated according to the process of the invention and the formulations of the present invention reduces the cholesterol and triglyceride levels in the body of an individual. They also facilitate the metabolism of minerals, nitrogen, bile acids and also shorten the transit time of digested blood materials through the gastro-intestinal tract.

The seed treated according to process of the present invention and formulations containing the treated seed do not increase calories and can also decrease the cholesterol level in the blood. Therefore, the debitterised powder of the seed of Fenugreek and formulations containing the debitterised powder of the seed can form an excellent dietary supplement for patients with diabetes and/or heart problems.

The invention is described in the examples given below which are provided by way of illustration only and therefore should not be construed to limit the scope of the invention.

EXAMPLE 1

Fenugreek seeds are cleaned to remove extraneous matters like stones, twigs, gunny bag threads, etc. The seeds which are brown colored and which are not totally dry and are discolored are separated and removed. Only light green or golden yellow colored seeds devoid of any unwanted organic materials are selected for debitterisation.

20 kgs of the cleaned Fenugreek seeds are ground to a mesh size in the range of 40–50 BSS. An extractor having a false bottom and a jacket surrounding the extractor is filled with filter cloth so as to allow free and slow percolation of the solvent passing through it. The ground seeds are loaded into the extractor. The solvent is then passed through the extractor so as to provide a slow and uniform wetting of the powder of the seeds. Steam is passed through the jacket surrounding the extractor so as to slowly warm the extractor to a temperature in the range of 75° C. to 80° C. The solvent is then removed from the extractor. The solvent is recirculated. The above process is continued until a clear extract is obtained.

In this experiment, a clear solution is obtained after six repeated extracts in a period of 10–12 hours. After the treatment is over, the powder is discharged, dried and ground.

The resulting product (20 kgs) is found to have no bitterness and can be used straightway as a fibrous supplementary food.

EXAMPLE 2

5 kgs of the fibrous supplementary food obtained in Example—1 and 4 kgs of guar gum, after removing all the external materials, are added into a blender. 1 kg of bran is also added to the blender and the entire mixture is blended for a period ranging from 30–40 minutes so as to obtain a uniform mixture.

130 g of malic acid is added to the blended mixture as a taste producer/enhancer and 25 g orange powder as a flavoring agent is also added. The blending is continued for a period ranging from 1–1.5 hours.

During the blending, samples were taken out every 20 minutes and tested for the taste of the blended mixture. Once the required taste is obtained, the blending process is stopped and the resulting product is dried, and if necessary packed in containers. 10 gms of the resulting product in 250 ml of water is found to form a gel with high viscosity. The fibrous content and the taste are found to be improved as compared to the treated seeds of Example 1.

EXAMPLE 3

6 kgs of Fenugreek seeds treated as in Example—1 having the mesh size of 60–80 BSS are placed in a blender. 3 kgs of guar gum are added and the mixture is blended to get an uniform extract. To this mixture, 1 kg of bran is added and blending is continued. 150 gms of malic acid as a taste producer agent is added to the resulting blend 30 mgs of a flavoring agent is added and 25 mg of tratraine as a coloring agent is also added. The blending is continued for another period of 1–1.5 hours.

During the blending, samples were drawn every 20 minutes and the taste and the quality of the resulting product is analyzed to confirm it is suitable for human consumption.

10 gms of the resulting product is dissolved in 240 ml of water and is found to form a gel and is found to be very tasty and easy to take as a daily fiber supplement. It is also found that the overall taste and the appearance is better than the product of Example—2.

EXAMPLE 4

8 kgs Fenugreek seeds treated as in Example—1 having the size 60–80 BSS and 1 kg of guar gum are added to a blender and they are blended to obtain a uniform mixture. To this blend, 1 kg of bran is added and the blending is continued. 200 gins of malic acid is added to the blend as a taste improver/enhancer and 40 gms of orange powder is added as a flavoring agent. The blending is continued for a period of 1–1.5 hours until a uniform blend is obtained.

The resulting blend is dried, and if necessary, is packed in suitable packets.

It is found that when 10 gm of this blend are dissolved in 240 ml of water, a gel is formed which can be easily taken as a supplementary fibrous food. The product is found to be tasty, good in appearance and lacking in bitterness.

Advantages of the invention are:
1. The debitterised seed powder as well as the formulations of the present invention are useful for providing soluble fiber for the body which is free from side effects.
2. The debitterised seed powder as well as the formulations containing it are useful in combating obesity and curtail the intake of calories.
3. The debitterised seed powder as well as formulations containing it help to prevent formation of carcinogenic effects in the colon.
4. The debitterised seed powder as well as formulations containing it helps to protect against heart attacks:
   a) by preventing absorption of cholesterol;
   b) increasing degradation of cholesterol;
   c) reducing triglycerides as well as enhancing the level of beneficial high density lipoprotein cholesterol.
5. The debitterised seed powder as well as the formulations containing it are useful in the control of diabetes by
   a) prolonging absorption of sugars b) facilitating uptake of glucose through muscles thereby facilitating utilization faster.

Another advantage of the invention is that the seed treated according to the present invention and formulations containing the debitterised seed powder have a minimal number of calories.

We claim:

1. A process for debitterisation of seed of Fenugreek (*Trigonella Foenumgraecum*) which comprises:
   a) soaking a powder of cleaned seed of Fenugreek (*Trigonella Foerumgraecum*) in a reactor vessel comprising an extractor containing filtering materials and having a jacket for passing steam, with one or more solvents able to extract compounds and components that cause bitterness from the powder;
   b) warming the reactor vessel slowly by passing steam through the jacket without contacting the powder in the extractor wherein the powder along with the one or more solvents which may remain with the powder is treated by passing steam through the jacket;
   c) removing the one or more solvents from the extractor;
   d) repeating steps a)–c) until the color of the solvent that is removed is same or nearly the same color as the one or more original solvents; and
   e) discharging the powder from the extractor.

2. A process as claimed in claim 1 wherein the solvent is selected from ethylene chloride, methylene chloride, acetone, hexane, alcohol, isopropylalcohol, or solvent ether.

3. A process according to claim 1 wherein the compounds and components that cause bitterness are Trigonelline alkoloid oil, resins and glycocides.

4. A process according to claim 1 wherein the solvent is able to extract fat from the powder.

5. A process as claimed in claim 1 wherein the filtering material is selected from coir, drill, cloth or materials embedded with cotton pads.

6. A process as claimed in claim 1 wherein the extraction is carried out for a period ranging from 8 to 12 hours.

7. The process according to claim 1 wherein the solvent is removed from the extractor and is recirculated into the extractor.

8. The process according to claim 1 wherein fresh solvent is used to soak the powder.

9. The process according to claim 1 where the powder of the cleaned seed is of a mesh size in the range of 30 to 50 BSS mesh.

10. The process according to claim 1 wherein the powder discharged from the extractor is dried and pulverised to a particle size ranging from 60 to 80 BSS mesh.

11. The process according to claim 1 wherein the reactor vessel is warmed to a temperature of 45° to 80° C.

12. The debitterised powder of the seed of the plant Fenugreek (*Trigonella Foenumgraecum*) prepared by the process as claimed in claim 1.

13. A formulation useful as a fibrous food supplement which comprises a mixture of the powder of the seed of the plant Fenugreek Foenumgraecum) prepared by the process as claimed in claim 1, guar gum and bran.

14. A formulation as claimed in claim 13 wherein the mount of the powder of the seed of the plant Fenugreek (*Trigonella Foenumgraecum*) ranges from 40–80% by weight.

15. A formulation as claimed in claim 13 wherein the mount of guar gum ranges from 15% to 30% by weight.

16. A formulation as claimed in claim 13 wherein the mount of the bran ranges from 5% to 10% by weight.

17. A formulation as claimed in claim 12 further comprising coloring agents, flavoring agents, taste improvers, vitamins, minerals and/or proteins.

18. A formulation as claimed in claim 13 wherein the moisture content ranges from 3% to 8% by weight.

19. A method of treating constipation comprising administering to a person in need thereof the powder of claim 12.

20. A method of treating constipation comprising administering to a person in need thereof a formulation of claim 13.

21. A method of introducing fiber into the diet comprising administering to a person the powder of claim 12.

22. A method of introducing fiber into the diet comprising administering to a person a formulation of claim 13.

23. A process for debitterisation of seed of Fenugreek (*Trigonella Foenumgraecum*) which comprises
   a) loading a powder of cleaned seed of Fenugreek (*Trigonella Foerumgraecum*) into a reactor vessel comprising an extractor containing filtering materials and having a jacket for passing steam;
   b) soaking the powder with one or more solvents able to extract compounds and components that cause bitterness from the powder by introducing the one or more solvents into the extractor to wet the powder;
   c) warming the reactor vessel slowly by passing steam through the jacket without contacting the powder in the extractor wherein the powder along with the one or more solvents which may remain with the powder is treated by passing steam through the jacket;
   d) separating the one or more solvents from the powder,
   e) repeating steps b)–d) until the solvent that is separated from the powder is same or nearly the same color as the one or more original solvents, and
   f) discharging the powder from the extractor.

* * * * *